(12) United States Patent
Min et al.

(10) Patent No.: US 11,034,642 B2
(45) Date of Patent: Jun. 15, 2021

(54) METHOD AND APPARATUS FOR CONTINUOUSLY RECOVERING (METH)ACRYLIC ACID

(71) Applicant: LG CHEM, LTD., Seoul (KR)

(72) Inventors: Yoon Jae Min, Daejeon (KR); Se Won Baek, Daejeon (KR); Jong Hun Song, Daejeon (KR); Jae Yul Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 26 days.

(21) Appl. No.: 16/553,733

(22) Filed: Aug. 28, 2019

(65) Prior Publication Data

US 2019/0382329 A1   Dec. 19, 2019

Related U.S. Application Data

(62) Division of application No. 16/079,790, filed as application No. PCT/KR2017/012620 on Nov. 8, 2017, now Pat. No. 10,487,036.

(30) Foreign Application Priority Data

Nov. 25, 2016   (KR) ........................ 10-2016-0158616

(51) Int. Cl.
*C07C 57/04* (2006.01)
*B01D 3/14* (2006.01)
(Continued)

(52) U.S. Cl.
CPC ................ *C07C 57/04* (2013.01); *B01D 3/00* (2013.01); *B01D 3/143* (2013.01); *B01D 11/04* (2013.01);
(Continued)

(58) Field of Classification Search
CPC .......... B01D 11/04; B01D 3/00; B01D 3/143; B01D 2257/70; B01D 2257/80; B01D 11/0488; B01D 11/0492; B01D 15/00; B01D 17/02; B01D 17/0202; B01D 2257/704; B01D 3/14; B01D 3/141; B01D 3/32; B01D 53/14; B01D 53/1406; B01D 53/1418; B01D 53/1456; B01D 2252/103;
(Continued)

(56) References Cited

U.S. PATENT DOCUMENTS 2,388,732 A * 11/1945 Finsterbusch ............ C10G 5/04
                                                    196/155
5,084,127 A    1/1992 Nakamura
(Continued)

FOREIGN PATENT DOCUMENTS

CN       1546453 A    11/2004
CN       1683309 A    10/2005
(Continued)

*Primary Examiner* — Joseph W Drodge
(74) *Attorney, Agent, or Firm* — Dentons US LLP

(57) ABSTRACT

The present invention relates to a continuous recovery method of (meth)acrylic acid and an apparatus for use in the recovery method. A continuous recovery method of (meth) acrylic acid according to the present invention can ensure a high recovery rate of (meth)acrylic acid through an acetic acid separation process in addition to enabling the stable recovery of (meth)acrylic acid and the operation of continuous processes.

3 Claims, 1 Drawing Sheet

(51) Int. Cl.
*B01D 11/04* (2006.01)
*C07C 51/44* (2006.01)
*C07C 51/48* (2006.01)
*B01D 53/14* (2006.01)
*B01D 3/00* (2006.01)
*C07C 51/50* (2006.01)

(52) U.S. Cl.
CPC ...... *B01D 11/0488* (2013.01); *B01D 53/1425* (2013.01); *B01D 53/1456* (2013.01); *C07C 51/44* (2013.01); *C07C 51/48* (2013.01); *C07C 51/50* (2013.01); *B01D 2257/70* (2013.01); *B01D 2257/80* (2013.01)

(58) Field of Classification Search
CPC . B01L 3/00; C07C 51/44; C07C 51/48; C07C 51/50; C07C 57/04; C07C 7/10; C07C 7/11; C07C 51/42; C07C 51/445; C07C 51/46; C07C 5057/04; Y02P 20/50
USPC ....... 210/511, 634, 638, 770; 96/155; 95/90, 95/141; 562/600
See application file for complete search history.

(56) References Cited

U.S. PATENT DOCUMENTS

| | | | |
|---|---|---|---|
| 5,246,790 A | 9/1993 | Mooney et al. | |
| 6,051,736 A * | 4/2000 | Schraut | C07C 51/42 562/532 |
| 6,399,817 B1 * | 6/2002 | Chapman | C07C 51/44 562/545 |
| 6,525,216 B1 * | 2/2003 | Nishimura | C07C 51/252 562/542 |
| 7,015,357 B2 | 3/2006 | Yada et al. | |
| 7,368,602 B2 | 5/2008 | Sakai et al. | |
| 9,517,997 B2 | 12/2016 | Baek et al. | |
| 9,718,756 B2 | 8/2017 | Baek et al. | |
| 9,962,625 B2 | 5/2018 | Baek et al. | |
| 10,029,976 B2 | 7/2018 | Gutermuth et al. | |
| 10,173,956 B1 * | 1/2019 | Song | C07C 51/44 |
| 10,610,803 B2 * | 4/2020 | Min | C07C 57/04 |
| 2003/0092937 A1 | 5/2003 | Wagner et al. | |
| 2007/0055079 A1 | 3/2007 | Yada et al. | |
| 2008/0228002 A1 * | 9/2008 | Aldrett-Lee | C07C 67/62 562/545 |
| 2008/0281124 A1 * | 11/2008 | Fauconet | C07C 51/42 562/600 |
| 2009/0124825 A1 * | 5/2009 | Tang | C07C 51/252 560/205 |
| 2010/0210871 A1 * | 8/2010 | Kobler | C07C 51/02 562/8 |
| 2010/0224478 A1 * | 9/2010 | Baek | C07C 51/42 203/42 |
| 2011/0036704 A1 * | 2/2011 | Blum | C07C 51/252 203/31 |
| 2013/0204050 A1 * | 8/2013 | Jevtic | C07C 29/149 568/885 |
| 2013/0317253 A1 | 11/2013 | Baek et al. | |
| 2015/0203431 A1 * | 7/2015 | Baek | C07C 51/43 562/600 |
| 2016/0075630 A1 | 3/2016 | Karime et al. | |
| 2016/0200656 A1 | 7/2016 | Song et al. | |
| 2016/0200657 A1 | 7/2016 | Song et al. | |
| 2020/0139263 A1 | 5/2020 | Min et al. | |

FOREIGN PATENT DOCUMENTS

| | | |
|---|---|---|
| CN | 1865216 A | 11/2006 |
| CN | 104470884 A | 3/2015 |
| CN | 105218355 A | 1/2016 |
| CN | 105263895 A | 1/2016 |
| CN | 105408296 A | 3/2016 |
| CN | 105473541 A | 4/2016 |
| EP | 1721884 A1 | 11/2006 |
| IN | 201817032457 | 5/2019 |
| JP | 41015569 B1 | 9/1966 |
| JP | 46030493 B1 | 9/1971 |
| JP | 3232678 B2 | 11/2001 |
| JP | 2005-247714 A | 9/2005 |
| JP | 2007217401 A | 8/2007 |
| JP | 2007521242 A | 8/2007 |
| JP | 3991873 B2 | 10/2007 |
| JP | 2009242285 A | 10/2009 |
| JP | 2009-263351 A | 11/2009 |
| JP | 5104275 B2 | 12/2012 |
| JP | 2013-151455 A | 8/2013 |
| JP | 2015-174851 A | 10/2015 |
| JP | 6036402 B2 | 11/2016 |
| KR | 10-0349602 B1 | 8/2002 |
| KR | 10-0375780 B1 | 8/2003 |
| KR | 10-2009-0041355 A | 4/2009 |
| KR | 10-0999428 B1 | 12/2010 |
| KR | 10-2012-0103520 A | 9/2012 |
| KR | 10-1546464 B1 | 8/2015 |
| KR | 10-1659541 B1 | 9/2016 |
| WO | 2012/124956 A2 | 9/2012 |

* cited by examiner

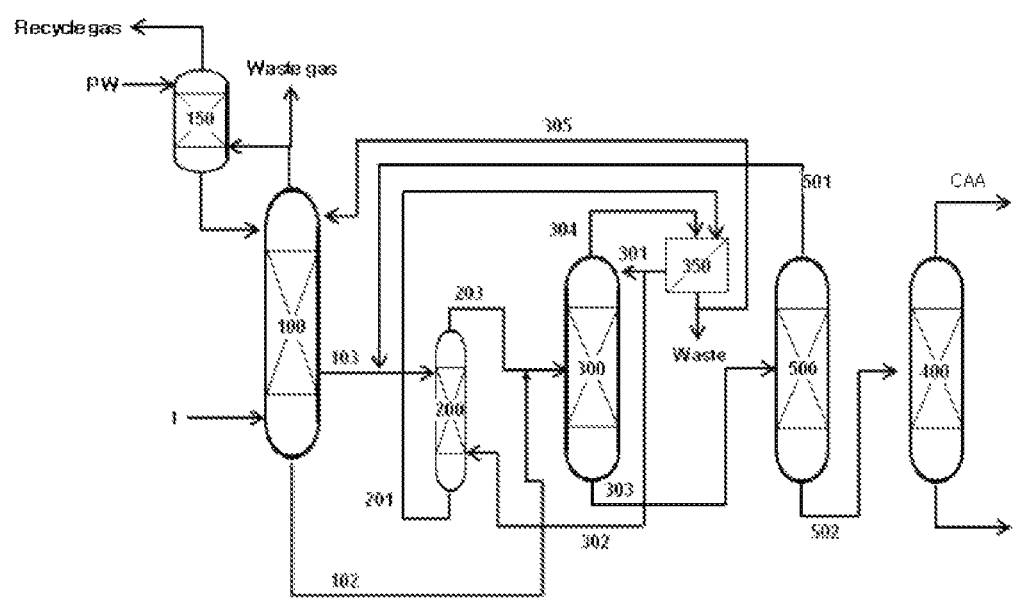

METHOD AND APPARATUS FOR CONTINUOUSLY RECOVERING (METH)ACRYLIC ACID

CROSS-REFERENCE TO RELATED APPLICATION

This application is a divisional of U.S. patent application Ser. No. 16/079,790 filed on Aug. 24, 2018, which is a U.S. National Stage of International Application No. PCT/KR2017/012620 filed on Nov. 8, 2017, and claims the benefit of priority from Korean Application No. 10-2016-0158616 filed on Nov. 25, 2016, all of which are hereby incorporated by reference in their entirety for all purposes as if fully set forth herein.

TECHNICAL FIELD

The present invention relates to a method of continuous recovery of (meth)acrylic acid and an apparatus for the method.

BACKGROUND OF ART (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a reaction product mixed gas including (meth)acrylic acid, non-reacted propane or propylene, (meth)acrolein, an inert gas, carbon dioxide, water vapor, and various organic by-products (acetic acid, heavies, and the like) is obtained in the back end of the reactor.

The (meth)acrylic acid-containing mixed gas contacts with an absorption solvent including water in a (meth)acrylic acid absorption tower, and is recovered as a (meth)acrylic acid aqueous solution. Further, a (meth)acrylic acid-stripped insoluble gas is recycled for a synthesis reaction of (meth)acrylic acid, and a part thereof is incinerated, converted into harmless gas, and discharged. The (meth)acrylic acid aqueous solution is extracted, distilled, and purified to obtain (meth)acrylic acid.

Meanwhile, various methods of controlling process conditions or a process sequence and the like to improve the recovery efficiency of (meth)acrylic acid have been suggested. Among them, a method is known wherein a part of the (meth)acrylic acid aqueous solution obtained in a (meth)acrylic acid absorption tower is fed to an extraction tower, a (meth)acrylic acid extract with reduced water content and the raffinate are obtained using a hydrophobic solvent, and the extract and the residue that is not fed to the extraction tower, among the (meth)acrylic acid aqueous solution obtained in the absorption tower, are distilled together.

Further, a method for reducing energy consumption is known, by selectively discharging an aqueous solution including (meth)acrylic acid of a low concentration at the middle stage of the absorption tower to obtain a high concentration (meth)acrylic acid aqueous solution at the lower part of the absorption tower, feeding the low concentration (meth)acrylic acid aqueous solution discharged at the middle stage of the absorption tower to the extraction tower, obtaining a (meth)acrylic acid extract with reduced water content and the raffinate using a hydrophobic solvent, and feeding the high concentration (meth)acrylic acid aqueous solution and the (meth)acrylic acid extract to the distillation tower and conducting azeotropic distillation.

However, according to the known method of continuous recovery of (meth)acrylic acid, if the amount of the hydrophobic solvent in the extraction tower is increased so as to increase the (meth)acrylic acid extraction rate, the amount of the azeotropic solvent subsequently fed to the feed stage of the water separation tower may increase, the amount of the solvent fed to the water separation tower should be constantly maintained for the azeotropic distillation of water and solvent so that the content of (meth)acrylic acid in the upper discharge liquid of the water separation tower may be low, and thus the amount of the solvent introduced into the water separation tower as reflux may decrease, and a change in gas/liquid behavior in the water separation tower may be generated. Thus, as the upper tray of the water separation tower is dried, the separation efficiency of the water separation tower may decrease, and (meth)acrylic acid recovery rate may decrease.

DETAILED DESCRIPTION OF THE INVENTION

Technical Problem

It is an object of the present invention to provide a method for continuous recovery of (meth)acrylic acid that can secure a high (meth)acrylic acid recovery rate, and simultaneously, can secure more improved operation stability.

It is another object of the present invention to provide an apparatus that can be used for the continuous recovery of (meth)acrylic acid.

Technical Solution

The present invention provides a method for continuous recovery of (meth)acrylic acid, including the steps of:

contacting a mixed gas including (meth)acrylic acid, organic by-products and water vapor, produced by the synthesis reaction of (meth)acrylic acid, with water in a (meth)acrylic acid absorption tower to obtain a (meth)acrylic acid aqueous solution of a low concentration discharged at any one point corresponding to 30 to 70% from the highest part of the absorption tower, and a (meth)acrylic acid aqueous solution of a high concentration discharged to the lowest stage of the absorption tower;

contacting the low concentration (meth)acrylic acid aqueous solution with an extraction solvent including a hydrophobic organic solvent in a (meth)acrylic acid extraction tower to extract (meth)acrylic acid;

distilling the obtained (meth)acrylic acid extract and high concentration (meth)acrylic acid aqueous solution in a water separation tower to obtain a distillate; and heating the feed excluding the distillate in the (meth)acrylic acid extract and high concentration (meth)acrylic acid aqueous solution in an acetic acid separation tower to obtain (meth)acrylic acid, wherein a weight ratio of the extraction solvent to water in the low concentration (meth)acrylic acid aqueous solution fed to the step of extracting (meth)acrylic acid is 2.7 or more, and the feed excluding the distillate in the (meth)acrylic acid extract and high concentration (meth)acrylic acid aqueous solution, introduced into the acetic acid separation tower, includes 0.1 to 10 wt % of acetic acid, 60 to 99 wt % of acrylic acid, and the remaining amount of organic by-products.

The present invention also provides an apparatus for continuous recovery of (meth)acrylic acid, including:

a (meth)acrylic acid absorption tower (100) equipped with a mixed gas inlet to which mixed gas including (meth) acrylic acid, organic by-products, and water vapor, produced by the synthesis reaction of (meth)acrylic acid, is fed, in which a low concentration (meth)acrylic acid aqueous solution outlet, at which a low concentration (meth)acrylic acid aqueous solution obtained by the contact of the mixed gas with water is discharged, is installed at any one point corresponding to 30 to 70% from the highest part, and a high concentration (meth)acrylic acid aqueous solution outlet is installed at the lowest stage;

a (meth)acrylic acid extraction tower (200) equipped with an aqueous solution inlet that is connected with the low concentration (meth)acrylic acid aqueous solution outlet of the absorption tower (100) through an aqueous solution transfer line (103), an extract outlet at which a (meth)acrylic acid extract obtained by the contact of the introduced (meth)acrylic acid aqueous solution with an extraction solvent is discharged, and a raffinate outlet at which a raffinate is discharged;

a water separation tower (300) equipped with a feed inlet that is connected with the extract outlet of the extraction tower (200) through an extract transfer line (203) and is connected with the (meth)acrylic acid aqueous solution outlet of the (meth)acrylic acid absorption tower (100) through a transfer line (102), an upper outlet at which the distillate of the introduced feed is discharged, and a lower outlet at which a feed excluding the distillate in the introduced feed is discharged; and an acetic acid separation tower (500) equipped with a feed inlet that is connected with the lower outlet of the water separation tower (300) through a transfer line (303), an outlet for acetic acid obtained by heating the introduced feed, and a (meth)acrylic acid outlet at which (meth)acrylic acid is discharged, wherein the apparatus is operated such that a weight ratio of the extraction solvent to water in the low concentration (meth)acrylic acid aqueous solution fed to the (meth)acrylic acid extraction tower (200) is 2.7 or more, and the feed introduced into the acetic acid separation tower includes 0.1 to 10 wt % of acetic acid, 60 to 99 wt % of acrylic acid, and the remaining amount of organic by-products.

Hereinafter, a method of continuous recovery of (meth) acrylic acid and a recovery apparatus according to the embodiments of the invention will be explained.

Unless otherwise described, terms used herein are defined as follows.

The term '(meth)acrylic acid' generally refers to acrylic acid, methacrylic acid, or a mixture thereof.

Further, the term '(meth)acrylic acid-containing mixed gas' generally refers to a mixed gas that may be produced when (meth)acrylic acid is prepared by gas phase oxidation. According to one embodiment of the present invention, the (meth)acrylic acid-containing mixed gas may be obtained by gas phase oxidation of at least one compound selected from the group consisting of propane, propylene, butane, i-butylene, t-butylene, and (meth)acrolein ('raw material compound') in the presence of a catalyst, wherein the (meth) acrylic acid-containing mixed gas may include (meth) acrylic acid, non-reacted raw material compounds, (meth) acrolein, an inert gas, carbon monoxide, carbon dioxide, water vapor, and various organic by-products (acetic acid, heavies, and the like), and the like. Herein, 'light ends' or 'heavies' are kinds of by-products that can be produced in the process of preparing and recovering (meth)acrylic acid, and generally refer to compounds having molecular weights that are smaller than or higher than that of (meth)acrylic acid.

The term 'feed' refers to a liquid mixture containing solute to be extracted, and it may be a mixture of a solute that is soluble in an extraction solvent and an inert material that is not soluble in an extraction solvent. Herein, if the extraction solvent is added to the feed, the solute is dissolved in the extraction solvent from the feed by mass transfer. Thereby, the extraction solvent in which a significant amount of solute is dissolved forms an extract, and the feed that is deprived of a significant amount of solutes forms a raffinate.

The term '(meth)acrylic acid aqueous solution' refers to an aqueous solution containing (meth)acrylic acid, and for example, it may be obtained by contacting the (meth)acrylic acid-containing mixed gas with water.

In addition, the technical terms used herein are only to mention specific embodiments, and are not intended to limit the invention. Further, singular forms used herein include plural forms, unless they have clearly opposite meanings, and the meaning of 'comprising' as used herein embodies a specific property, area, integer, step, operation, element, or component, and it does not exclude the addition of other specific properties, areas, integers, steps, operations, elements, or components.

Hereinafter, referring to the attached drawings, specific embodiments of the invention will be explained in detail so that one of ordinary knowledge in the art may easily practice it. However, the present invention may be embodied in various forms, and is not limited to the examples.

I. A Method of Continuous Recovery of (Meth)Acrylic Acid

According to one embodiment of the invention, a method for continuous recovery of (meth)acrylic acid is provided, including the steps of:

contacting a mixed gas including (meth)acrylic acid, organic by-products, and water vapor, produced by the synthesis reaction of (meth)acrylic acid, with water in a (meth)acrylic acid absorption tower to obtain a (meth) acrylic acid aqueous solution of a low concentration discharged at any one point corresponding to 30 to 70% from the highest part of the absorption tower, and a (meth)acrylic acid aqueous solution of a high concentration discharged to the lowest stage of the absorption tower;

contacting the low concentration (meth)acrylic acid aqueous solution with an extraction solvent including a hydrophobic organic solvent in a (meth)acrylic acid extraction tower to extract (meth)acrylic acid;

distilling the obtained (meth)acrylic acid extract and high concentration (meth)acrylic acid aqueous solution in a water separation tower to obtain a distillate; and heating the feed excluding the distillate in the (meth) acrylic acid extract and high concentration (meth)acrylic acid aqueous solution in an acetic acid separation tower to obtain (meth)acrylic acid, wherein a weight ratio of the extraction solvent to water in the low concentration (meth)acrylic acid aqueous solution fed to the step of extracting (meth)acrylic acid is 2.7 or more, and the feed excluding the distillate in the (meth) acrylic acid extract and high concentration (meth)acrylic acid aqueous solution, introduced into the acetic acid separation tower, includes 0.1 to 10 wt % of acetic acid, 60 to 99 wt % of acrylic acid, and the remaining amount of organic by-products.

The present inventors confirmed during studies on the continuous recovery method of (meth)acrylic acid that, in the previously disclosed (meth)acrylic acid recovery method wherein a (meth)acrylic acid aqueous solution is fed to an extract tower, a (meth)acrylic acid extract is obtained using a hydrophobic solvent, and the extract is distilled to recover (meth)acrylic acid, and if the amount of the hydrophobic solvent is increased so as to increase the extraction rate, many problems may occur such as an increase in the content of acetic acid in the lower stage of the water separation tower, and a resulting decrease in the recovery rate.

Thus, as a result of continuous studies by the present inventors, it was confirmed that if an acetic acid separation process is introduced after the distillation process of (meth)acrylic acid, the water separation tower may be operated at a low temperature to minimize the content of acetic acid, and the acetic acid remaining in the lower stage of the water separation tower may be recovered from the acetic acid tower and reused, and thus a more economical and stable continuous process can be operated.

Hereinafter, referring to FIG. 1, each process that can be included in the embodiments of the invention will be explained.

Absorption Process

First, the continuous recovery method of (meth)acrylic acid according to one embodiment includes the step of contacting a mixed gas including (meth)acrylic acid, organic by-products, and water vapor, produced by the synthesis reaction of (meth)acrylic acid, with water in a (meth)acrylic acid absorption tower to obtain the aqueous solution of (meth)acrylic acid, and an absorption process throughout the specification means a process for obtaining the aqueous solution of (meth)acrylic acid.

More specifically, the synthesis reaction of (meth)acrylic acid may be conducted by the oxidation reaction of at least one compound selected from the group consisting of propane, propylene, butane, isobutylene, and (meth)acrolein in the presence of a gas phase catalyst. Herein, the gas phase oxidation reaction may be progressed using a gas phase oxidation reactor of a common structure and under common reaction conditions. As the catalyst for the gas phase oxidation reaction, common catalysts may be used, and for example, catalysts suggested in Korean Registered Patent No. 0349602 and No. 037818 and the like may be used. In the (meth)acrylic acid-containing mixed gas produced by the gas phase oxidation reaction, in addition to the desired product, (meth)acrylic acid, non-reacted raw material compounds, intermediate (meth)acrolein, an inert gas, carbon dioxide, vapor, and various organic by-products (acetic acid, light ends, heavies, and the like) may be included.

Referring to FIG. 1, the (meth)acrylic acid aqueous solution may be obtained in the form of an aqueous solution in which (meth)acrylic acid is dissolved, by feeding a (meth)acrylic acid-containing mixed gas (1) to a (meth)acrylic acid absorption tower (100), to contact it with an absorption solvent, water.

Herein, the kind of the (meth)acrylic acid absorption tower (100) may be determined considering contact efficiency of the mixed gas (1) with the absorption solvent, and the like. As non-limiting examples, the (meth)acrylic acid absorption tower (100) may be a packed column type or a multistage tray type. Inside the packed column type absorption tower, a filler such as a Raschig ring, a pall ring, a saddle, gauze, structured packing, and the like may be applied.

Considering the efficiency of the absorption process, the mixed gas (1) may be fed to the lower part of the absorption tower (100), and the solvent including water may be fed to the upper part of the absorption tower (100).

The absorption solvent may include water such as tap water, deionized water, and the like, and it may include recycled process water introduced from other processes (for example, an aqueous phase recycled from an extraction process and/or a distillation process). In the absorption solvent, a trace amount of organic by-products introduced from other processes (for example, acetic acid) may be included. However, considering the absorption efficiency of (meth)acrylic acid, it is preferable that organic by-products may be included in a content of 15 wt % or less in the absorption solvent fed to the absorption tower (100) (particularly, in the recycled process water).

Meanwhile, the (meth)acrylic acid absorption tower (100) may be operated at an internal pressure of 1 to 1.5 bar or 1 to 1.3 bar, and an internal temperature of 50 to 100° C. or 50 to 80° C., considering the water content according to saturated water vapor pressure and the condensation conditions of (meth)acrylic acid, and the like.

Through the absorption process, a low concentration (meth)acrylic acid aqueous solution having about 50 wt % or less of (meth)acrylic acid is discharged to any one point corresponding to 30 to 70% from the highest part of the (meth)acrylic acid absorption tower (100), and a high concentration (meth)acrylic acid aqueous solution having about 50% or more of (meth)acrylic acid is discharged to the lowest stage. Further, (meth)acrylic acid stripped non-condensable gas is discharged to the upper stage of the absorption tower.

The obtained (meth)acrylic acid aqueous solutions of a low concentration and a high concentration may be fed to a water separation tower (300) through a transfer line (102) of a high concentration (meth)acrylic acid aqueous solution, or may be fed to a (meth)acrylic acid extraction tower (200) through a transfer line (103) of a low concentration (meth)acrylic acid aqueous solution, as shown in FIG. 1.

Meanwhile, at least a part of the non-condensable gas discharged to the upper part of the (meth)acrylic acid absorption tower (100) may be fed to a process for recovering organic by-products (particularly, acetic acid) included in the non-condensable gas, and the remainder may be fed to a waste gas incinerator and discarded. That is, according to one embodiment of the invention, a process of contacting the non-condensable gas with an absorption solvent to recover acetic acid included in the non-condensable gas may be progressed.

The process of contacting the non-condensable gas with an absorption solvent may be conducted in an acetic acid absorption tower (150). Herein, for effective absorption of acetic acid, the acetic acid absorption tower (150) may be operated at the internal pressure of 1 to 1.5 bar, or 1 to 1.3 bar, and at the internal temperature of 50 to 100° C., or 50 to 80° C. In addition, specific operation conditions of the acetic acid absorption tower (150) may follow the disclosure of Korean Laid-Open Patent Publication No. 2009-0041355.

Here, an absorption solvent (process water) for absorbing acetic acid may be fed to the upper part of the acetic acid absorption tower (150), and an acetic acid-containing aqueous solution may be discharged to the lower part of the acetic acid absorption tower (150). Further, the acetic acid-containing aqueous solution may be fed to the upper part of the (meth)acrylic acid absorption tower (100) and used as an absorption solvent. The acetic acid-stripped non-condensable gas may be cycled to the synthesis reaction process of (meth)acrylic acid and reused.

Extraction Process

The continuous recovery method of (meth)acrylic acid according to one embodiment includes the step of contacting the low concentration (meth)acrylic acid aqueous solution with an extraction solvent including a hydrophobic organic solvent in a (meth)acrylic acid extraction tower to extract (meth)acrylic acid.

The low concentration (meth)acrylic acid aqueous solution fed to the extraction tower (200) contacts an extraction solvent, and is discharged as an extract in which a significant amount of (meth)acrylic acid is dissolved and a raffinate that is deprived of a significant amount of (meth)acrylic acid, respectively. Here, the low concentration (meth)acrylic acid aqueous solution is discharged at any one point corresponding to 30 to 70% from the highest part of the (meth)acrylic acid absorption tower, and it may include 1 to 50 wt % of (meth)acrylic acid, 50 to 95 wt % of water, and the remaining amount of organic by-products.

In the extraction tower (200), the extract that is a relatively light phase is obtained through the upper outlet, and the raffinate that is a relatively heavy phase is obtained through the lower outlet of the extraction tower. Before the raffinate is discharged from the extraction tower (200), a certain amount thereof remains stationary at a stationary section of the lower part of the extraction tower, and a part thereof is discharged to the lower outlet of the extraction tower.

As such, by contacting the low concentration (meth) acrylic acid aqueous solution with an extraction solvent in the extraction tower (200), most water included in the low concentration (meth)acrylic acid aqueous solution may be removed. Thereby, a treatment load of the subsequent distillation process may be lowered, thus improving energy efficiency of the total process. Furthermore, by lowering the treatment load of the distillation process, polymerization of (meth)acrylic acid that may be generated during distillation may be minimized, to secure more improved recovery efficiency of (meth)acrylic acid.

The extraction solvent fed to the extraction tower (200) includes a hydrophobic organic solvent, and organic by-products may be included therein. Specifically, the extraction solvent may include one or more hydrophobic organic solvents selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

The weight ratio of the extraction solvent to water in the low concentration (meth)acrylic acid aqueous solution fed to the step of extracting (meth)acrylic acid may be 2.7 or more, preferably 3.0 or more, and more preferably 3.0 to 5.0. As such, by controlling the amount of the extraction solvent used in the extraction process, the reflux of the solvent may be increased in the subsequent distillation process, thereby further increasing the recovery rate of (meth)acrylic acid.

In the extraction process, if the weight ratio of the extraction solvent to water in the low concentration (meth) acrylic acid aqueous solution is less than 2.7, (meth)acrylic acid extraction efficiency may be lowered, which is not preferable. Further, if the weight ratio of the extraction solvent to water in the low concentration (meth)acrylic acid aqueous solution is greater than 5.0, although the extraction efficiency may be improved as the weight ratio of the extraction solvent to water in the (meth)acrylic acid aqueous solution increases, (meth)acrylic acid loss may increase in the subsequent distillation process, and in order to prevent this, the reflux of the solvent may excessively increase, which is not preferable.

As the extraction tower (200), common extraction towers of liquid-liquid contact type may be used without specific limitations. As non-limiting examples, the extraction tower (200) may be a Karr type of reciprocating plate column, a rotary-disk contactor, a Scheibel column, a Kuhni column, a spray extraction tower, a packed extraction tower, a pulsed packed column, and the like.

Through such an extraction process, a (meth)acrylic acid extract is discharged to the upper part of the extraction tower (200), and the discharged extract is fed to the water separation tower (300) through a transfer line (203). In addition, a raffinate is discharged to the lower part of the extraction tower (200), and the discharged raffinate is fed to a phase separation tank (350) through a transfer line (201), treated, and recycled.

Herein, in the extract, in addition to a desired compound, (meth)acrylic acid, an extraction solvent, water, and organic by-products may be included. According to one embodiment, under a steady state where stable operation is conducted, 5 to 13 wt % of (meth)acrylic acid, 85 to 93 wt % of an extraction solvent, 0.01 to 2 wt % of water, and the remaining amount of organic by-products may be included in the extract. That is, most water included in the (meth) acrylic acid aqueous solution may be recovered as a raffinate through the extraction process. As most water is recovered from the extraction tower (200), a distillation load of a distillation process may be reduced to lower energy consumption. Further, since distillation conditions may be relaxed, polymerization of (meth)acrylic acid may be minimized in the distillation process, thus securing operation stability and improving recovery efficiency of (meth)acrylic acid.

The raffinate discharged from the extraction tower (200) may consist mostly of water, and a part of non-extracted (meth)acrylic acid and by-products may be included therein. However, according to one embodiment of the invention, a very small amount, such as 15 wt % or less, or 0.1 to 5 wt %, of (meth)acrylic acid may be included in the raffinate, thus minimizing the loss of (meth)acrylic acid in the absorption process and extraction process.

Distillation Process

The method for continuous recovery of (meth)acrylic acid according to one embodiment includes the step of distilling the obtained (meth)acrylic acid extract and the high concentration (meth)acrylic acid aqueous solution in a water separation tower to obtain a distillate.

In the step of obtaining a distillate, the operation temperature of at least one point within 10% from the lowest stage of the water separation tower may be 40 to 80° C., preferably 40 to 70° C. It is preferable that in the step of obtaining a distillate, the organic by-products (acetic acid) included in the (meth)acrylic acid extract and the high concentration (meth)acrylic acid aqueous solution are not distilled, but only water and solvents are distilled, and that the organic by-products (acetic acid) are separated in the acetic acid separation tower described below, and for this, it is required to control the temperature of at least one point within 10% from the lowest stage of the water separation tower as described above.

The water separation tower (300) of one embodiment may have a pressure of the highest stage of atmospheric pressure to 20 torr, and an operation temperature of the lowest stage of 40 to 100° C.

In order to achieve efficient distillation, it is preferable that the extract and high concentration (meth)acrylic acid aqueous solution are fed to any one stage corresponding to 25 to 75%, or 40 to 60%, from the highest stage of the water separation tower, based on the total number of stages of the water separation tower.

If the extract and the high concentration (meth)acrylic acid aqueous solution are fed to a point exceeding 75% from the highest stage of the water separation tower (300), a part of the water to be recovered as the upper discharge liquid of the water separation tower that is included in the extract and the high concentration (meth)acrylic acid aqueous solution, and the extraction solvent, may be included in the lower discharge liquid of the water separation tower, and they should be recovered in the acetic acid separation tower, thus making the operation complicated. If they are fed to the point less than 25% from the highest stage of the water separation tower, the concentration of acrylic acid included in the upper discharge liquid of the water separation tower may increase, and thus the acrylic acid recovery rate of the water separation tower may be lowered.

The extract and the high concentration (meth)acrylic acid aqueous solution fed to the water separation tower (300) are made to come in contact with an azeotropic solvent introduced into the upper part, and heated to an optimum temperature, thereby achieving distillation by evaporation and condensation.

Herein, in order to effectively separate (meth)acrylic acid included in the extract and the high concentration (meth) acrylic acid aqueous solution from the remaining components (for example, water, acetic acid, extraction solvents, and the like), the distillation is preferably conducted by azeotropic distillation.

A solvent used for the azeotropic distillation is preferably a hydrophobic azeotropic solvent that may form an azeotrope with water and acetic acid, and may not form an azeotrope with (meth)acrylic acid. The hydrophobic azeotropic solvent preferably has a lower boiling point than that of (meth)acrylic acid (for example, a boiling point of 120° C. or less, 10 to 120° C., or 50 to 120° C.).

Specifically, the hydrophobic azeotropic solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Considering production efficiency according to a continuous process, it is preferable that the hydrophobic azeotropic solvent is identical to the extraction solvent of the extraction process. As such, if the same kinds of solvents are used in the extraction process and the distillation process, at least a part of the solvent that is distilled in the water separation tower (300) and recovered through a phase separation tank (350) may be fed to the (meth)acrylic acid extraction tower (200) and reused as an extraction solvent.

Through the distillation process, among the feed, components other than (meth)acrylic acid are discharged to the upper part of the distillation tower (300) together with the azeotropic solvent, and (meth)acrylic acid is discharged to the lower part of the distillation tower (300).

The upper discharge liquid of the water separation tower (300) may be fed to the phase separation tank (350) and reused after a predetermined treatment. Herein, the phase separation tank (350) is an apparatus for separating immiscible liquids by gravity or centrifugal force and the like, wherein a relatively light liquid (for example, an organic phase) may be recovered from the upper part of the phase separation tank (350), and a relatively heavy liquid (for example, an aqueous phase) may be recovered from the lower part of the phase separation tank (350).

For example, the upper discharge liquid of the water separation tower (300), and the raffinate discharged in the above-explained extraction tower (200), may be separated into an organic phase including a solvent and an aqueous phase including water, in the phase separation tank (350). The separated organic phase may be fed to the upper part of the water separation tower (300) and used as an azeotropic solvent. If necessary, at least a part of the organic phase may be fed to the extraction tower (200) and used as an extraction solvent. Further, at least a part of the aqueous phase separated in the phase separation tank (350) may be fed to the (meth)acrylic acid absorption tower (100) and used as an absorption solvent, and a part thereof may be treated as waste water. In the aqueous phase, acetic acid may be partly included, and the concentration of acetic acid included in the aqueous phase may vary according to the kind of azeotropic solvents and reflux ratio and the like.

Meanwhile, while the (meth)acrylic acid aqueous solution passes through the (meth)acrylic acid absorption tower (100), the extraction tower (200), and the water separation tower (300) and the like, at least a part of (meth)acrylic acid included in the aqueous solution may form dimers or oligomers. To minimize such polymerization of (meth)acrylic acid, common polymerization inhibitors may be added to the water separation tower (300).

Acetic Acid Separation Process

The continuous recovery method of (meth)acrylic acid includes the step of heating the feed excluding the distillate in the (meth)acrylic acid extract and high concentration (meth)acrylic acid aqueous solution in an acetic acid separation tower to obtain (meth)acrylic acid.

The feed excluding the distillate in the (meth)acrylic acid extract and high concentration (meth)acrylic acid aqueous solution is fed to the acetic acid separation tower (500) through the transfer line (303). Further, by supplying heat through the reboiler at the lower stage of the acetic acid separation tower, acetic acid is recovered through the upper outlet, and (meth)acrylic acid excluding the recovered acetic acid is obtained through the lower outlet.

The feed excluding the distillate in the (meth)acrylic acid extract and high concentration (meth)acrylic acid aqueous solution, introduced in the acetic acid separation tower, includes 0.1 to 10 wt % of acetic acid, 60 to 99 wt % of acrylic acid, and the remaining amount of organic by-products, and it may further include extraction solvents or water.

Here, in order to achieve efficient acetic acid separation, it is preferable that the feed is fed to any one stage corresponding to 40 to 70%, or 50 to 70%, from the highest stage of the acetic acid separation tower, based on the total number of stages of the acetic acid separation tower.

The acetic acid separation tower may have a temperature of the upper part of 40 to 90° C., and a temperature of the lower part of 50 to 100° C. The "upper part" of the acetic acid separation tower means at least any one point within 10% from the highest stage of the acetic acid separation tower, and the "lower part" means at least any one point within 10% from the lowest stage of the acetic acid separation tower.

For efficient distillation of the feed of the acetic acid separation tower, the pressure of the highest stage may be controlled to atmospheric pressure to 20 torr.

Meanwhile, the upper discharge liquid obtained at the upper stage by heating the feed excluding the distillate in the (meth)acrylic acid extract and high concentration (meth)acrylic acid aqueous solution in the acetic acid separation tower may be introduced into the (meth)acrylic acid extraction tower and recycled.

In addition, (meth)acrylic acid obtained by heating the feed excluding the distillate in the (meth)acrylic acid extract and high concentration (meth)acrylic acid aqueous solution in the acetic acid separation tower may include 4 wt % or less, or 3 wt % or less, of acetic acid.

As explained, according to the continuous recovery method of (meth)acrylic acid, acetic acid is separately recovered through the acetic acid separation tower, and fed to the (meth)acrylic acid extraction tower and recycled, thus enabling the operation of a more economical and stable continuous process.

In the lower discharge liquid of the acetic acid separation tower (500), in addition to (meth)acrylic acid, heavies such as a polymer of (meth)acrylic acid, polymerization inhibitors, and the like may be included. Thus, if necessary, a step of feeding the lower discharge liquid of the acetic acid separation tower (500) to a heavies separation tower (400) and separating heavies included in the lower discharge liquid may be further conducted. Crude (meth)acrylic acid (CAA) recovered through the process may be passed through an additional crystallization process and obtained as high purity (meth)acrylic acid (HPAA). Herein, the heavies separation process, the crystallization process, and the like may be conducted under common conditions, and the process conditions are not specifically limited.

In the method of continuous recovery of (meth)acrylic acid, each of the above-explained steps may be conducted organically and continuously. In addition to the above-explained steps, processes that can be commonly conducted before, after, or simultaneously with each step may be further included.

II. An Apparatus for Continuous Recovery of (Meth)Acrylic Acid

According to another embodiment of the invention, an apparatus for continuous recovery of (meth)acrylic acid is provided, including:

a (meth)acrylic acid absorption tower (100) equipped with a mixed gas inlet to which a mixed gas including (meth)acrylic acid, organic by-products, and water vapor, produced by the synthesis reaction of (meth)acrylic acid, is fed, in which a low concentration (meth)acrylic acid aqueous solution outlet, at which a low concentration (meth)acrylic acid aqueous solution obtained by the contact of the mixed gas with water is discharged, is installed at any one point corresponding to 30 to 70% from the highest part, and a high concentration (meth)acrylic acid aqueous solution outlet is installed at the lowest stage;

a (meth)acrylic acid extraction tower (200) equipped with an aqueous solution inlet that is connected with the low concentration (meth)acrylic acid aqueous solution outlet of the absorption tower (100) through an aqueous solution transfer line (103), an extract outlet at which a (meth)acrylic acid extract obtained by the contact of the introduced (meth)acrylic acid aqueous solution with an extraction solvent is discharged, and a raffinate outlet at which the raffinate is discharged;

a water separation tower (300) equipped with a feed inlet that is connected with the extract outlet of the extraction tower (200) through an extract transfer line (203) and is connected with the (meth)acrylic acid aqueous solution outlet of the (meth)acrylic acid absorption tower (100) through a transfer line (102), an upper outlet at which the distillate of the introduced feed is discharged, and a lower outlet at which a feed excluding the distillate in the introduced feed is discharged; and an acetic acid separation tower (300) equipped with a feed inlet that is connected with the lower outlet of the water separation tower (300) through a transfer line (303), an outlet of acetic acid obtained by heating the introduced feed, and a (meth)acrylic acid outlet at which (meth)acrylic acid is discharged, wherein the apparatus is operated such that the weight ratio of the extraction solvent to water in the low concentration (meth)acrylic acid aqueous solution fed to the (meth)acrylic acid extraction tower (200) is 2.7 or more, and the feed introduced into the acetic acid separation tower, includes 0.1 to 10 wt % of acetic acid, 60 to 99 wt % of acrylic acid, and the remaining amount of organic by-products.

That is, in the apparatus of one embodiment, basically, the (meth)acrylic acid absorption tower (100) is connected with the (meth)acrylic acid extraction tower (200) through the transfer line (103) of the low concentration (meth)acrylic acid aqueous solution. In addition, the (meth)acrylic acid extraction tower (200) is connected to the water separation tower (300) through the (meth)acrylic acid extract transfer line (203), and the water separation tower (300) is connected with the acetic acid separation tower (500) through the transfer line (303) of the feed excluding the distillate in the extract.

Particularly, in the apparatus for continuous recovery of (meth)acrylic acid of one embodiment, the outlet of the low concentration (meth)acrylic acid aqueous solution is positioned at any one point corresponding to 30 to 70% from the highest part of the (meth)acrylic acid absorption tower (100), and the outlet of the high concentration (meth)acrylic acid aqueous solution is positioned at the lowest stage.

A feed inlet that is connected with the extract outlet of the extraction tower (200) through the transfer line (203), and is connected with the (meth)acrylic acid aqueous solution outlet of the (meth)acrylic acid absorption tower (100) through the transfer line (102), may be positioned at any one stage corresponding to 25 to 75% from the highest stage of the water separation tower, based on the total number of stages of the water separation tower (300).

Further, in the apparatus, a feed inlet that is connected with the lower outlet of the water separation tower (300) through the transfer line (303) may be positioned at any one stage corresponding to 40 to 70% from the highest stage of the acetic acid separation tower, based on the total number of stages of the acetic acid separation tower (500).

The (meth)acrylic absorption tower (100) may be a packed column type, or a multistage tray type, and inside of the packed column type tower, fillers such as a Raschig ring, a pall ring, a saddle, gauze, structured packing, and the like may be applied.

As the (meth)acrylic acid extraction tower (200), common extraction towers of a liquid-liquid contact type may be used without specific limitation. As non-limiting examples, the extraction tower may be a Karr type of reciprocating plate column, a rotary-disk contactor, a Scheibel column, a Kuhni column, a spray extraction tower, a packed extraction tower, a pulsed packed column, and the like.

In addition, the water separation tower (300) and the acetic acid separation tower (500) may be packed columns including the above-described fillers thereinside, or a multistage column, preferably equipped with a sieve tray column, or a dual flow tray column, and the like.

In addition, the acetic acid absorption tower (150), (meth)acrylic acid aqueous solution transfer line (103), the extract transfer line (203), the phase separation tank (350), the heavies separation tower (400), and the like, as shown in FIG. 1, may have constructions common in the technical field to which the invention pertains.

Advantageous Effects

The continuous recovery method of (meth)acrylic acid according to the present invention can secure a high (meth) acrylic acid recovery rate, and simultaneously enables stable (meth)acrylic acid recovery and the operation of a continuous process, through the acetic acid separation.

BRIEF DESCRIPTION OF THE DRAWINGS

FIG. 1 schematically shows the method and apparatus for continuous recovery of (meth)acrylic acid according to one embodiment of the present invention.

DETAILED DESCRIPTION OF THE EMBODIMENTS

Hereinafter, preferable examples are presented to aid in understanding of the invention. However, these examples are only to illustrate the invention, and the scope of the invention is not limited thereto.

Examples

Using the apparatus with the construction of FIG. 1, the process for continuously recovering acrylic acid was conducted as follows.

(Extraction Process)

Among the acrylic acid aqueous solution of a low concentration (103) discharged to the side part of the absorption tower (100) (composition: acrylic acid 21.06 wt %, acetic acid 4.15 wt %, and water 74.79 wt %), acrylic acid was extracted using toluene introduced through an extraction solvent transfer line (302) according to a liquid-liquid contact method. The extract (203) was discharged to the upper part of the extraction tower (200), and the raffinate was discharged to the lower part of the extraction tower and it may be recycled to the highest part of the acrylic acid absorption tower (100) through the raffinate transfer line (201).

As the acrylic acid extraction tower (200), a Karr type of reciprocating plate column having a total 56 of stages with an inner diameter of 22 mm was used. The acrylic acid aqueous solution of a low concentration (103) discharged to the side part of the absorption tower (100) was introduced through the highest stage, i.e., the first stage of the extraction tower (200), at a flow rate of 23.8 g/min. Further, a part of the reflux flow including toluene obtained as an organic layer in the upper discharge liquid of the water separation tower (300) was used as the extraction solvent (composition: acrylic acid at about 0.27 wt %, acetic acid at about 0.48 wt %, the balance being toluene) of the extraction tower (200), wherein the extraction solvent was introduced through the lowest stage, i.e., the 56th stage of the extraction tower (200), at a flow rate of 59.44 g/min.

After stable operation was conducted, under a steady state, an acrylic acid extract (composition: toluene at about 91.32 wt %, acrylic acid at about 7.42 wt %, water at about 0.62 wt %, and acetic acid at about 0.64 wt %) was obtained at the upper part of the extraction tower (200) at a flow rate of 64.59 g/min, and the remaining raffinate (composition: water at about 93.36 wt %, acrylic acid at about 2.03 wt %, and acetic acid at about 4.61 wt %) was discharged to the lower part of the extraction tower (200).

As a result of operating the acrylic acid extraction tower (200), the water removal rate for the low concentration acrylic acid aqueous solution discharged from the side part of the acrylic acid absorption tower was 97.8%, and the acrylic acid extraction rate was 92.7%. Here, the ratio of the extraction solvent introduced into the extraction tower/water was 3.3.

(Distillation Process)

As the water separation tower (300), a sieve tray (including a down corner) column having a total of 39 stages with an inner diameter of 70 mm was used, and the operation pressure was maintained at 110 torr. The upper discharge liquid (203) of the extraction tower (200) of the extraction process and the lower discharge liquid (102) of the acrylic acid absorption tower (100) were introduced into the 20th stage from the water separation tower (300), at the flow rates of 55.06 g/min and 34.41 g/min, respectively. Further, a part of the toluene reflux flow separated in the phase separation tank (350) was introduced into the highest stage, i.e., the first stage of the water separation tower (300), at a flow rate of 25.96 g/min, as an azeotropic solvent.

Heat was supplied through the reboiler of the lower stage of the water separation tower (300) to control such that the temperature of the 35th stage of the water separation tower became 50° C. or less. After stable operation was conducted for about 6 hours, under a steady state, to the upper part of the water separation tower (300), the distillate consisting of an organic phase and an aqueous phase was discharged at 31.80 g/min and 0.45 g/min, respectively, and acrylic acid flow to the lower part of the water separation tower (300) was 47.22 g/min. Here, under a steady state, the upper temperature of the water separation tower (300) was maintained at 39.2° C., and the lower temperature was maintained at 88.2° C. An organic phase distillate (304) exhibited a composition of 0.07 wt % of acrylic acid, 0.02 wt % of acetic acid, and 99.91 wt % of toluene, and the lower flow (303) of the water separation tower exhibited a composition of 92.53 wt % of acrylic acid, 2.53 wt % of acetic acid, and 4.94 wt % of toluene. The acrylic acid recovery rate of the water separation tower (300) was 99.7%.

(Acetic Acid Separation Process)

As the acetic acid separation tower (500), a dual flow tray column having a total of 15 stages with an inner diameter of 20 mm was used, and the operation pressure was maintained at 80 torr. The lower flow (303) of the water separation tower (300) was introduced into the 9th stage from the upper part of the acetic acid separation tower (500) at a flow rate of 5.1 g/min. A part of the upper flow of the acetic acid separation tower (500) was introduced into the highest stage, i.e., the first stage of the acetic acid separation tower (500), at a flow rate of 5.2 g/min, as reflux.

By supplying heat through the reboiler at the lower stage of the acetic acid separation tower (500), the distillate was controlled to 10 wt % based on the feed introduction amount. After conducting stable operation for about 5 hours, under a steady state, 0.51 g/min of distillate was discharged to the upper part of the acetic acid separation tower (500), and 4.59 g/min of acrylic acid flow was obtained at the lower part of the acetic acid separation tower (500). Here, the temperature of the upper part of the acetic acid separation tower (500) was maintained at 53° C., and the temperature of the lower part was maintained at 85° C. Under a steady state, the upper flow (501) of the acetic acid separation tower exhibited a composition of acrylic acid at 23.62 wt %, acetic acid at 24.38 wt %, and toluene at 52.00 wt %, and the lower flow (502) of the acetic acid separation tower exhibited a composition of acrylic acid at 97.72 wt %, acetic acid at 1100 ppm, and heavies and polymerization inhibitor at 2.28 wt %. The acrylic acid recovery rate of the acetic acid separation tower (500) was 97.4%.

Comparative Example

A process for continuous recovery of acrylic acid was conducted by the same method as in the example, except that a distillation process described below was conducted, without the acetic acid separation process.

(Distillation Process)

As the water separation tower (300), a sieve tray (including a down corner) column having a total of 39 stages with an inner diameter of 70 mm was used, and the operation pressure was maintained at 110 torr. The lower discharge liquid (102) of the acrylic acid absorption tower (100) and the upper extract (203) of the extraction tower (200) of Example 1 were introduced into the 20th stage from the upper part of the water separation tower (300) at 44.99 g/min and 36.4 g/min, respectively. In addition, a part of the toluene reflux flow separated from the phase separation tank (350) was introduced into the highest stage, i.e., the first stage of the water separation tower (300), at a flow rate 22.22 g/min. Here, the mass ratio of the toluene in the reflux introduced into the upper part of the water separation tower and the toluene in the upper extract (203) of the extraction tower introduced into the feed introduction stage of the water separation tower was 0.66:1.

Heat was supplied through the reboiler of the lower stage of the water separation tower (300) to control such that the temperature of the feed introduction stage became 64.6° C., and the temperature of the 15th stage did not exceed about 46° C. After stable operation was conducted for about 6 hours, under a steady state, the distillate consisting of an organic phase and an aqueous phase was discharged to the upper part of the water separation tower (300) at 33.86 g/min and 8.50 g/min, respectively, and at the lower part of the water separation tower (300), acrylic acid flow was obtained at 39.03 g/min. Here, under a steady state, the temperature of the upper part of the water separation tower (300) was maintained at 42.4° C., and the temperature of the lower part was maintained at 92.3° C. The organic phase distillate (304) exhibited a composition of 0.73 wt % of acrylic acid, 0.76 wt % of acetic acid, and 98.51 wt % of toluene, and the lower flow (303) of the water separation tower exhibited a composition of 98.15 wt % of acrylic acid, 3000 ppm of acetic acid, and 1.85 wt % of acrylic acid polymer and polymerization inhibitor. The acrylic acid recovery rate of the water separation tower (300) was 98.7%.

REFERENCE NUMERALS

1: (meth)acrylic acid-containing mixed gas
100: (meth)acrylic acid absorption tower
102: high concentration (meth)acrylic acid aqueous solution transfer line
103: low concentration (meth)acrylic acid aqueous solution transfer line
150: acetic acid absorption tower
200: (meth)acrylic acid extraction tower
201: raffinate transfer line
203: extract transfer line
300: water separation tower
301: azeotropic solvent transfer line
302: extraction solvent transfer line
303: lower flow of the water separation tower
304: upper flow of the water separation tower
305: absorption solvent (water) transfer line
350: phase separation tank
400: heavies separation tower
500: acetic acid separation tower
501: upper flow of acetic acid separation tower
502: (meth)acrylic acid transfer line

The invention claimed is:

1. An apparatus for continuous recovery of (meth)acrylic acid, comprising:
   a (meth)acrylic acid absorption tower equipped with a mixed gas inlet to which a mixed gas feed comprising (meth)acrylic acid, organic by-products, and water vapor, produced by a synthesis reaction of (meth)acrylic acid, is fed, in which a low concentration (meth)acrylic acid aqueous solution outlet, at which a low concentration (meth)acrylic acid aqueous solution obtained by contact of the mixed gas with water is discharged, is installed at a position that is 30% to 70% lower than a highest point of the (meth)acrylic acid absorption tower, and a high concentration (meth)acrylic acid aqueous solution outlet, at which a high concentration (meth)acrylic acid aqueous solution is discharged, is installed at a lowest stage of a plurality of stages, wherein the low concentration (meth)acrylic acid aqueous solution comprises 50 wt % or less of (meth)acrylic acid and the high concentration (meth)acrylic acid aqueous solution comprises 50 wt % or more of (meth)acrylic acid;
   a (meth)acrylic acid extraction tower equipped with an aqueous solution inlet that is connected with the low concentration (meth)acrylic acid aqueous solution outlet of the (meth)acrylic acid absorption tower through an aqueous solution transfer line, an extract outlet at which a (meth)acrylic acid extract obtained by contact of the (meth)acrylic acid aqueous solution, which is input from the (meth)acrylic acid absorption tower through the aqueous solution transfer line, with an extraction solvent is discharged, and a raffinate outlet at which a raffinate is discharged;
   a water separation tower equipped with a feed inlet that is connected with the extract outlet of the (meth)acrylic acid extraction tower through an extract transfer line and is connected with the (meth)acrylic acid aqueous solution outlet of the (meth)acrylic acid absorption tower through a transfer line, an upper outlet at which a distillate of the mixed gas feed is discharged, and a lower outlet at which a feed of the mixed gas feed excluding the distillate is discharged;
   an acetic acid separation tower equipped with a feed inlet that is connected with the lower outlet of the water separation tower through a transfer line, an acetic acid outlet at which acetic acid obtained by heating the mixed gas feed excluding the distillate feed, which is input from the lower outlet of the water separation tower through the transfer line, is discharged, and a (meth)acrylic acid outlet at which (meth)acrylic acid is discharged, and
   a heavies separation tower equipped with an inlet that is connected to the (meth)acrylic acid outlet of the acetic acid separation tower,
   wherein the apparatus is operated such that a weight ratio of the extraction solvent to water in the low concentration (meth)acrylic acid aqueous solution fed to the (meth)acrylic acid extraction tower is 2.7 or more, and the feed introduced into the acetic acid separation tower comprises 0.1 wt % to 10 wt % of acetic acid, 60 wt % to 99 wt % of acrylic acid, and a remaining amount of organic by-products.

2. The apparatus according to claim 1, wherein the feed inlet that is connected with the extract outlet of the extraction tower through an extract transfer line and is connected with the (meth)acrylic acid aqueous solution outlet of the (meth)acrylic acid absorption tower through a transfer line is positioned at a stage that is 25% to 75% lower than a first top stage of the water separation tower, based on a total number of stages of the water separation tower.

3. The apparatus according to claim 1, wherein the feed inlet that is connected with the lower outlet of the water separation tower through a transfer line is positioned at a stage that is 40% to 70% lower than a first top stage of the acetic acid separation tower, based on a total number of stages of the acetic acid separation tower.

* * * * *